(12) United States Patent
Karinka et al.

(10) Patent No.: US 7,501,053 B2
(45) Date of Patent: Mar. 10, 2009

(54) BIOSENSOR HAVING IMPROVED HEMATOCRIT AND OXYGEN BIASES

(75) Inventors: Shridhara Alva Karinka, Lowell, MA (US); W. James Scott, Bedford, MA (US)

(73) Assignee: Abbott Laboratories, Abbott Park, IL (US)

( * ) Notice: Subject to any disclaimer, the term of this patent is extended or adjusted under 35 U.S.C. 154(b) by 643 days.

(21) Appl. No.: 10/278,657

(22) Filed: Oct. 23, 2002

(65) Prior Publication Data

US 2004/0079653 A1    Apr. 29, 2004

(51) Int. Cl.
    *G01N 27/327* (2006.01)
(52) U.S. Cl. ............... 205/792; 205/777.5; 204/403.14; 204/403.11; 204/403.04
(58) Field of Classification Search ........................ 204/403.01–403.14; 205/777.5, 792
    See application file for complete search history.

(56) References Cited

U.S. PATENT DOCUMENTS

| | | | |
|---|---|---|---|
| 5,147,806 A * | 9/1992 | Kamin et al. ............... | 436/149 |
| 5,708,247 A | 1/1998 | McAleer et al. ........ | 204/403.05 |
| 5,951,836 A | 9/1999 | McAleer et al. .......... | 205/777.5 |
| 6,134,461 A | 10/2000 | Say et al. .................... | 600/345 |
| 6,271,045 B1 | 8/2001 | Douglas et al. ............. | 436/518 |
| 6,284,125 B1 | 9/2001 | Hodges et al. .............. | 205/775 |
| 6,287,451 B1 | 9/2001 | Winarta et al. ........... | 205/777.5 |

FOREIGN PATENT DOCUMENTS

| | | |
|---|---|---|
| EP | 1 146 332 | 10/2001 |
| WO | 98/35225 | 8/1998 |
| WO | 99/19507 | 4/1999 |
| WO | 9919507 | 4/1999 |

OTHER PUBLICATIONS

Hilt et al. (Transition Metal Complexes of 1, 10-Phenantrholine-5,6-dione as Efficient Mediators for the Regeneration of NAD+ i Enzymatic Synthesis, J. Chem. Sol., Chem. Commun., 1993, 1706-1707) ("Hilt").*
Pages 93-95 of vol. 9 of the 4th edition of the Kirk-Othmer Encyclopedia of Chemical Technology, John Wiley & Sons, 1994.*

(Continued)

*Primary Examiner*—Alex Noguerola
(74) *Attorney, Agent, or Firm*—Edward J. Baba; Bozicevic, Field & Francis LLP

(57) ABSTRACT

A biosensor that utilizes a mediator, i.e., an isomer of phenanthroline quinone, 1,10-phenanthroline-5,6-dione, and a metal ion, such as manganese, with an enzyme dependent upon $NAD(P)^+$, such as, for example, glucose dehydrogenase, for improving the hematocrit bias and oxygen bias of biosensors. The electrodes of the biosensors employing this mediator and a metal ion provide an accurate clinical response over a hematocrit range that ranges from about 20% to about 70% and over an oxygen tension range that ranges from about 1 kPa to about 20 kPa.

19 Claims, 4 Drawing Sheets

OTHER PUBLICATIONS

Rivera et al. ("Ruthenium complexes as redox mediators for malate and lactate dehydrogenases," Bioelectrochemistry and Bioenergetics, 34(1994) 169-175).*

Fernandez ("Reagentless carbon paste phosphate biosensors: preliminary studies," Sensors and Actuators B 47 (1998) 13-20).*

Hedenmo et al. ("Reagentless Ampermometric Glucose Dehydrogenase Biosensor Based on Electrocatalytic Oxidation of NADH by Osmium Phenanthroline Mediator," Analyst, Dec. 1996, vol. 121 (1891-1895)).*

Wu, et al. "Electrocatalytic Oxidation of NADH at Glassy Carbon Electrodes Modified with Transition Metal Complexes Containing 1,10-Phenanthroline—5, 6-dione Ligands." Analytical Chemistry, vol. 68, No. 20. Oct. 15, 1996.

PCT Search Report for PCT/US03/33532 mailed Apr. 26, 2004.

G. A. Shabir, et al., "Method development and validation for determining the identity, assay and purity of 1, 10 -phenanthroline-5,6-dione by HPLC and LC-MS."

* cited by examiner

BIOSENSOR HAVING IMPROVED HEMATOCRIT AND OXYGEN BIASES

BACKGROUND OF THE INVENTION

1. Field of the Invention

This invention relates to biosensors, and, more particularly, to biosensors for determining the concentration of an analyte in a biological sample.

2. Discussion of the Art

All biosensors for determining the concentration of analytes in a sample of blood suffer from hematocrit sensitivity to some degree. The biosensor response decreases as the hematocrit of the sample increases. There is no single reason for this decrease in the signal, though some of the reasons include diminished diffusion of the analyte in the sample and increased solution resistance. One of the methods proposed for the elimination of hematocrit sensitivity is to filter the red cells from the sample. The membrane technology to filter red cells increases both the assay time and measurement imprecision. Oxygen sensitivity has presented a challenge. Biosensors employing the enzyme glucose dehydrogenase are not expected to be oxygen sensitive. However, the oxidation-reduction reactions of the mediator (or coenzyme) could involve free radical intermediates. When these intermediates have long lifetimes, molecular oxygen can quench them, thereby rendering the chemistry sensitive to oxygen tension.

U.S. Pat. Nos. 5,708,247 and 5,951,836 describe a disposable glucose test strip for use in a test meter of the type that receives a disposable test strip and a sample of blood from a patient and performs an electrochemical analysis. The working formulation comprises a filler, an enzyme effective to oxidize glucose, e.g., glucose oxidase, and a mediator effective to transfer electrons from the enzyme. The working formulation is printed over a conductive base layer to form a working electrode. The filler, for example, a silica filler, is selected to have a balance of hydrophobicity and hydrophilicity such that on drying it forms a two-dimensional network on the surface of the conductive base layer. The response of this test strip is claimed to be temperature independent over relevant temperature ranges and is substantially insensitive to the hematocrit of the patient.

In photometric biosensors, a membrane is typically used to separate red cells from a sample of whole blood. The use of a membrane increases the time of response. U.S. Pat. No. 6,271,045 describes a photometric biosensor that employs a correction method to compensate for hematocrit sensitivity. The biosensor comprises a support member that contains a spreading layer and a reagent layer, and a capillary tube in communication with the support layer and spreading layer for transporting a sample of body fluid thereto. A capillary tube is provided on the support member whereby a fluid containing an analyte to be tested is introduced into the tube and flows through the tube to the spreading layer and contacts the reagent layer. In order to compensate for hematocrit level in the case of whole blood, additional sensors can be implemented so that they inspect the capillary tube in the test device, one sensor at the beginning of the capillary channel and one at the end. In this biosensor, whole blood is applied to the capillary channel. The entry flow of whole blood is timed as it moves between sensors. The time that the blood takes to travel the length of the capillary tube is an indication of the hematocrit of the blood. That information is used to correct any shift in reflectance readings of the instrument caused by the hematocrit level. It is also known that the absorbance of hemoglobin can be measured, and the measurement can be used to account for the sensitivity of the measurement to hemoglobin.

The majority of electrochemical biosensors do not use membrane technology; hence, electrochemical biosensors suffer from hematocrit sensitivity. U.S. Pat. No. 6,284,125 describes a biosensor insensitive to hematocrit, where red cells are separated from plasma. U.S. Pat. No. 6,287,451 describes a biosensor that can employ a method in which hematocrit level can be measured electrochemically, and the corrected concentration of an analyte can be determined from the measured concentration of the analyte along with factors that depend on the sensitivity of the biosensor to hematocrit level. The magnitude of the hematocrit sensitivity is dependent on the type of biosensor and on the type of measurement. For example, if the reaction is allowed to go to completion, the lengthy reaction time allows for complete oxidation of the analyte in the sample, thereby making the measurement less sensitive to hematocrit.

U.S. Ser. No. 09/529,617, filed Jun. 7, 2000, incorporated herein by reference, describes $NAD^+$-dependent and $NAD(P)^+$-dependent enzymes having substrates of clinical value, such as glucose, D-3-hydroxybutyrate, lactate, ethanol, and cholesterol. Amperometric electrodes for detection of these substrates and other analytes can be designed by incorporating this class of enzymes and establishing electrical communication with the electrodes via the mediated oxidation of the reduced cofactors NADH and NADPH. $NAD^+$-dependent glucose dehydrogenase can be used as the enzyme and 1,10-phenanthroline-5,6-dione isomer can be used as the mediator. This combination shows hematocrit sensitivity and oxygen sensitivity. The enzyme is not dependent on oxygen (oxygen does not act as a co-substrate as it does with glucose oxidase) and hence is expected to be insensitive to oxygen. However, the mediator reaction appears to be slow and hence is affected by the presence of oxygen. The mediation reaction involves free radical intermediates. If the reaction is slow, the free radical intermediates have longer half-life; hence, the probability of being quenched by molecular oxygen is high. Accordingly, the enzyme mediator combination shows oxygen dependency. The hematocrit bias of 1,10-phenanthroline-5,6-dione mediator is not clearly understood; however, it is speculated that the slow reaction rate of the mediator is responsible for significant hematocrit sensitivity. 4,7-Phenanthroline-5,6-dione does not exhibit as much sensitivity to variations in hematocrit or oxygen as does 1,10-phenanthroline-5,6-dione. However, the structure of 1,10-phenanthroline-5,6-dione renders it easier to synthesize than does the structure of 4,7-phenanthroline-5,6-dione. The starting materials for the synthesis of 1,10-phenanthroline-5,6-dione are much less expensive than are the starting materials for 4,7-phenanthroline-5,6-dione. Additionally, the reaction conditions for the synthesis of 1,10-phenanthroline-5,6-dione are much less severe than are the reaction conditions for 4,7-phenanthroline-5,6-dione. Accordingly, it would be desirable to reduce the sensitivity of 1,10-phenanthroline-5,6-dione to hematocrit sensitivity and oxygen sensitivity.

Glucose monitoring devices are calibrated at normal hematocrit. In samples having a lower hematocrit, the biosensor reads a higher than appropriate blood glucose level, and in samples having a higher hematocrit, the biosensor reads a lower than appropriate blood glucose level.

SUMMARY OF THE INVENTION

This invention involves a biosensor that utilizes a mediator, i.e., an isomer of phenanthroline quinone, 1,10-phenanthroline-5,6-dione, and at least one metal ion selected from the group consisting of a transition metal ion, such as, for example, manganese, iron, osmium, ruthenium, and the like, and heavier alkaline earth metal ion, such as, for example, calcium, barium, and the like, with an enzyme dependent upon $NAD(P)^+$, such as, for example, glucose dehydrogenase, for improving the hematocrit bias and oxygen bias of the biosensor. The electrodes of the biosensors employing this mediator and the foregoing metal ion provide an accurate clinical response over a hematocrit range that ranges from about 20% to about 70% and over an oxygen tension range that ranges from about 1 kPa to about 20 kPa.

Although oxidation of glucose catalyzed by glucose dehydrogenase is not oxygen sensitive, the mediator can be sensitive to oxygen. The 1,10-phenanthroline-5,6-dione mediator has the structural formula:

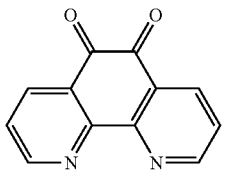

The use of 1,10-phenanthroline-5,6-dione mediator in a glucose biosensor is described in U.S. Ser. No. 09/529,617, filed Jun. 7, 2000, incorporated herein by reference In one aspect, this invention provides a biosensor in the form of a strip, wherein the biosensor has a working electrode comprising a working ink comprising a $NAD(P)^+$-dependent enzyme, 1,10-phenanthroline-5,6-dione as a mediator, and at least one metal ion selected from the group consisting of a transition metal ion and heavier alkaline earth metal ion. In one embodiment, the biosensor contains an electrode arrangement comprising two electrodes. The biosensor comprises:

an electrode support;
a first electrode disposed on the electrode support, the first electrode comprising a working area, the working area comprising a working ink deposited on an electrically conductive material; and
a dual-purpose reference/counter electrode disposed on the electrode support, the dual-purpose reference/counter electrode being spaced apart from the first electrode.

In another embodiment, the biosensor contains an electrode arrangement comprising three electrodes. The biosensor comprises:

(a) an electrode support;
(b) a first electrode disposed on the electrode support, the first electrode being a working electrode, the working electrode comprising a working ink deposited on an electrically conductive material;
(c) a second electrode disposed on the electrode support, the second electrode being a reference electrode; and
(d) a third electrode disposed on the electrode support, the third electrode being a counter electrode, the counter electrode comprising an electrically conductive material.

The invention described herein provides a mediator that is substantially insensitive to either hematocrit or oxygen, thereby enabling the use of this mediator in hospital and retail markets, where samples having extreme hematocrit ranges (20% to 70%) and oxygen tensions (neonatal, venous, capillary and arterial) are encountered. A biosensor in the form of a strip employing this mediator can be used for numerous analytes, such as, for example, glucose, ketone bodies, lactate, and alcohol.

The invention described herein exhibits several advantages/benefits as compared with other biosensors that are being used for similar purposes. These advantages/benefits include:

1. elimination of the requirement of a membrane or any cross-linked network;
2. the ability to employ a kinetic measurement, and consequently, the elimination of the requirement to drive the reaction to completion, thereby eliminating the hematocrit sensitivity;
3. the selection of an appropriate reagent combination—enzyme/mediator/metal or enzyme/metal complex of the mediator—is responsible for lower hematocrit sensitivity;
4. the catalytic and electrochemical activity of the mediator/metal combination or metal complex of the mediator is responsible for oxygen and hematocrit insensitivity.
5. improved performance is related to the choice of the combination of mediator and metal ion.

DETAILED DESCRIPTION

Figure 1:
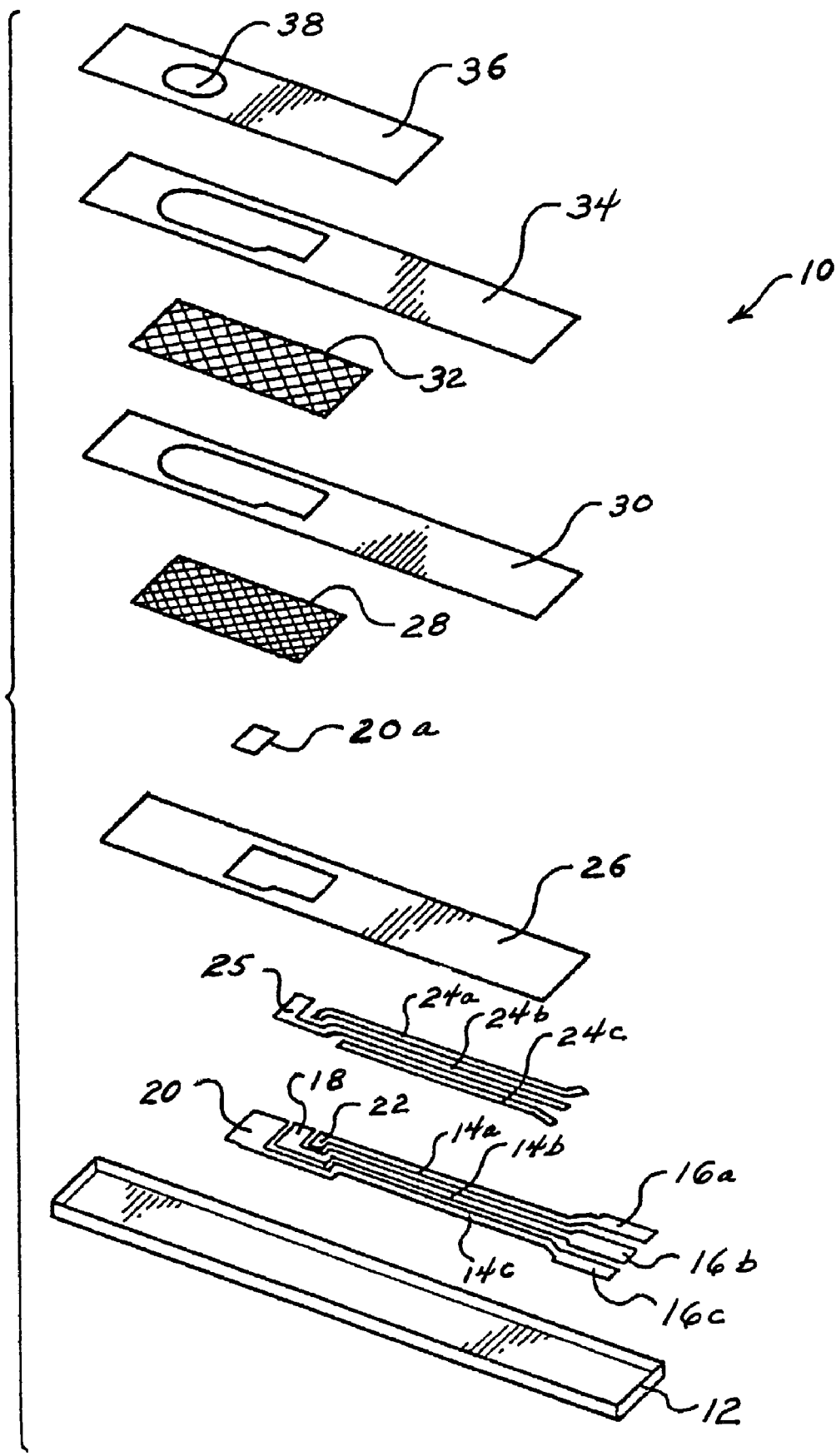
FIG. 1 is a schematic diagram that illustrates a perspective view of a biosensor strip having a working electrode and a dual-purpose reference/counter electrode.

As used herein, the expression "transition metal" means those elements of a metallic nature that have partially filled d or f shells in any of their commonly occurring oxidation states. The expression "heavier alkaline earth metals" means those elements of a metallic nature that are in the IIA column of the periodic table and that have an atomic number equal to or higher than 20.

The structural formula of the mediator 1,10-phenanthroline-5,6-dione is shown below:

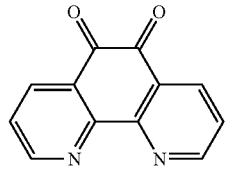

When the mediator is reduced by the enzyme, dimers or oligomers or both are formed on account of intermolecular hydrogen bonding between reduced 1,10-phenanthroline-5,6-dione molecules. These oligomers are not soluble in the reaction medium and hence are not readily regenerated for continued mediation. Intermolecular hydrogen bonding of a dimer of reduced 1,10-phenanthroline-5,6-dione is shown below.

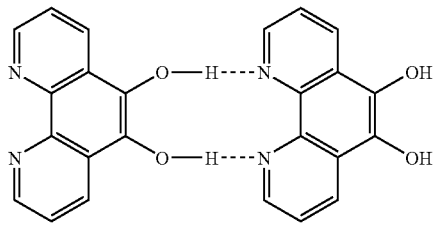

The dimerization or oligomerization can be minimized in several ways. The nitrogen atoms can be blocked by chemical modification. A substituent, e.g., an alkyl group, can be added to one or both of the nitrogen atoms in order to prevent the formation of hydrogen bonds. Preventing the formation of hydrogen bonds also increases the solubility of the mediator in both the oxidized and reduced form. The methyl derivative of 1,10-phenanthroline-5,6-dione shows increased solubility. The compound mediates the oxidation of NADH in the biosensor strip, as described in U.S. Ser. No. 09/529,617, filed Jun. 7, 2000, incorporated herein by reference. The following structural formula illustrates mono-alkylated 1,10-phenanthroline-5,6-dione, where R represents an alkyl group, such as, for example, —$CH_3$ and X represents an anion such as $BF_4^-$:

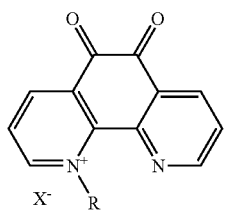

Synthesis of alkylated compounds requires several steps. The alkyl group is introduced after the 1,10-phenanthroline-5,6-dione is formed. The oxidation-reduction properties of alkylated 1,10-phenanthroline-5,6-dione may not be dependent on metal ion concentration, which would indicate that the alkylation process has inhibited the formation of intermolecular hydrogen bonds.

The nitrogen atoms can also be blocked by the formation of a complex having a coordination bond between a ligand and a metal ion. Complexes can be formed prior to being used in a formulation in the strip; alternatively, metal ions can simply be mixed with the ink formulation that contains the mediator. The metal ions preferred for this invention include, but are not limited to, manganese, zinc, calcium, iron, ruthenium, cobalt, osmium, nickel, copper, rhenium, rhodium, iridium, chromium, technetium, barium, strontium. The binding efficiencies in these complexes are dependent on the particular metal ion employed. For example, Mn (II) ions provide stronger binding than do Mg (II) ions. A metal complex of 1,10-phenanthroline-5,6-dione is shown below.

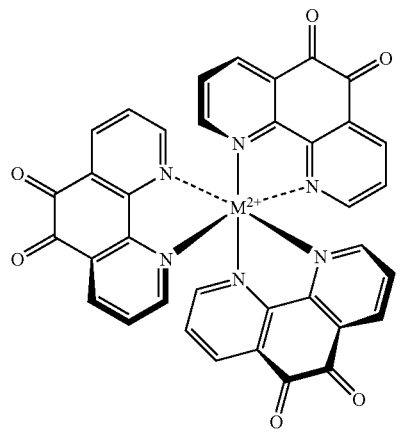

The generic formula of the complex cation is shown below. The ligands a, b, c, and d can represent two 1,10-phenanthroline-5,6-dione molecules or other monodentate ligands, such as, for example, chloride, water, ammonia, or the like, or multidentate ligands, such as, for example, bipyridyl or the like.

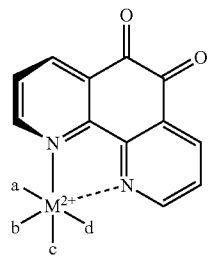

Figure 2:
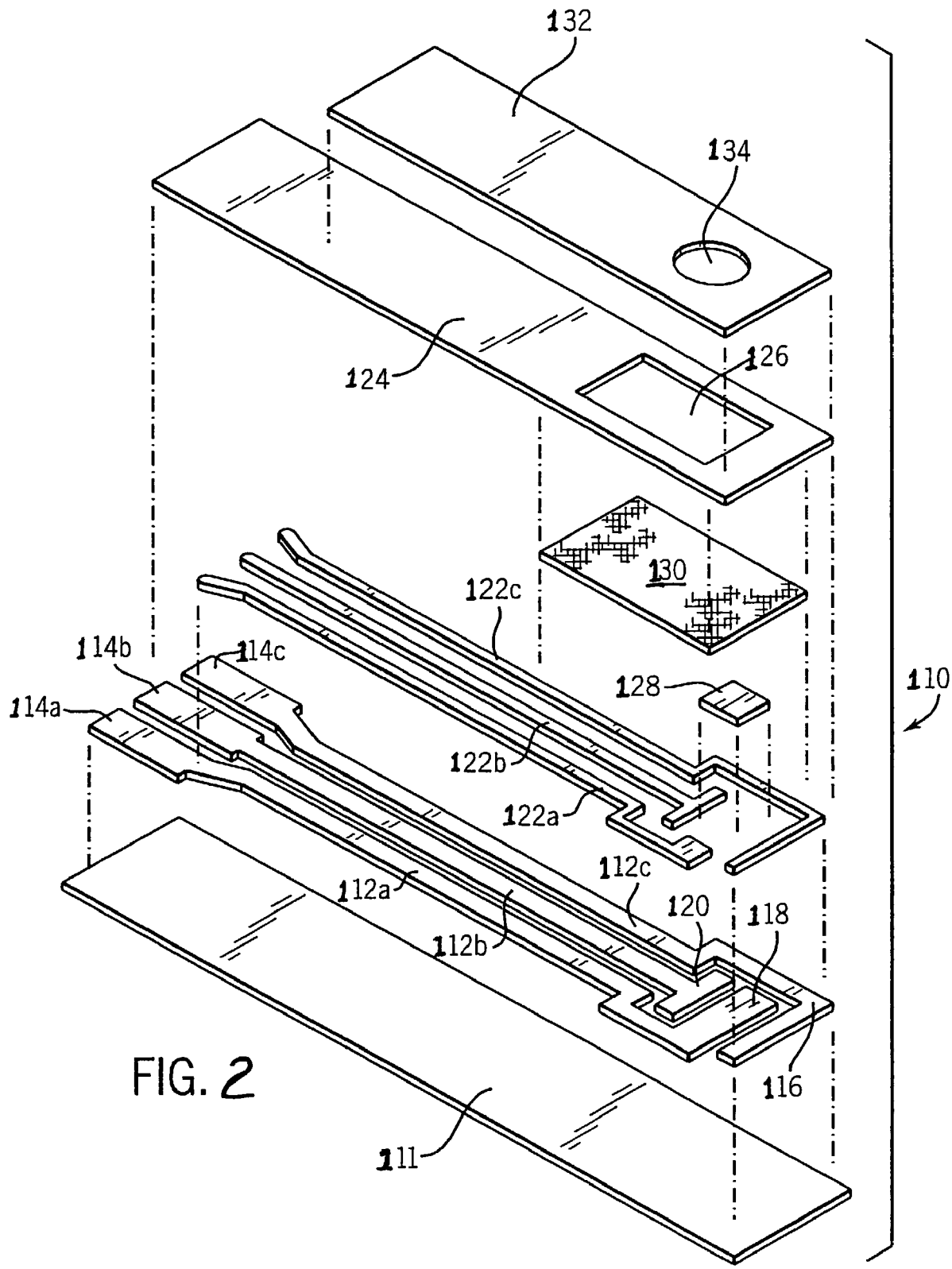
FIG. 2 is a schematic diagram that illustrates a perspective view of a biosensor strip having a working electrode, a reference electrode, and a counter electrode.

A biosensor strips suitable for this invention are illustrated in FIGS. 1 and 2. Referring to FIG. 1, a biosensor strip 10 comprises an electrode support 12, preferably an elongated strip of polymeric material (e.g., polyvinyl chloride, polycarbonate, polyester, or the like) supports three tracks 14a, 14b, and 14c of electrically conductive ink, preferably comprising carbon. These tracks 14a, 14b, and 14c determine the positions of electrical contacts 16a, 16b, and 16c, a dual-purpose reference/counter electrode 18, a working electrode 20, and a trigger electrode 22. The electrical contacts 16a, 16b, and 16c can be inserted into an appropriate measurement device (not shown) for measurement of current.

Each of the elongated portions of the conductive tracks 14a, 14b, and 14c can optionally be overlaid with a track 24a, 24b, and 24c of conductive material, preferably made of a mixture comprising silver particles and silver chloride particles. The enlarged exposed area 25 of track 24b overlies the dual-purpose reference/counter electrode 18. A layer of a hydrophobic electrically insulating material 26 further overlies the tracks 14a, 14b, and 14c. The positions of the dual-purpose reference/counter electrode 18, the working electrode 20, the trigger electrode 22, and the electrical contacts 16a, 16b, and 16c are not covered by the layer of hydrophobic electrically insulating material 26. This hydrophobic electrically insulating material 26 serves to prevent short circuits. Because this insulating material is hydrophobic, it can cause the sample to be restricted to the exposed electrodes. A preferred insulating material is commercially available as "POLYPLAST" (Sericol Ltd., Broadstairs, Kent, UK).

Optionally, a first layer of mesh 28, a second insulating layer 30, a second layer of mesh 32, a third insulating layer 34, and a tape 36 can overlay the hydrophobic insulating material. The tape 36 includes a small aperture 38 to allow access of the applied sample to the underlying layers of mesh 28 and 32. The second insulating layer 30 and the third insulating layer 34 include openings to allow access of the applied sample to the underlying layers of mesh 28 and 32.

The working electrode 20 comprises a layer of conductive material containing a working area 20a. The working area 20a is formed from a working ink, which is printed on the layer of conductive material of the working electrode 20. The working ink comprises a mixture of an oxidation-reduction mediator, a metal ion, an enzyme, and, optionally, a conductive material.

The working area 20a is formed from a printing ink that includes a mixture of an enzyme, an oxidation-reduction mediator, a metal ion, and, optionally, a conductive material. Alternatively, instead of an enzyme, the working area 20a can contain a substrate that is catalytically reactive with an enzyme to be assayed. The respective printing inks are applied to the working electrode 20 and the dual-purpose reference/counter electrode 18 as discrete areas of fixed length. In a preferred embodiment, the conductive material comprises particles of carbon and the oxidation-reduction mediator comprises 1,10-phenanthroline-5,6-dione.

A printing ink comprises an aqueous suspension of the conductive material, a redox mediator, and a metal ion. For the working electrode 20, the printing ink also includes an enzyme. For example, when the analyte to be measured is glucose in blood, the enzyme is preferably glucose dehydrogenase, and the redox mediator is preferably a 1,10-phenanthroline-5,6-dione. In the alternative, for the working electrode 20, the printing ink can include a substrate in lieu of an enzyme when the analyte to be measured is an enzyme.

The printing inks can be screen-printed. The printing inks can further include a polysaccharide (e.g., a guar gum or an alginate), a hydrolyzed gelatin, an enzyme stabilizer (e.g., glutamate or trehalose), a film-forming polymer (e.g., a polyvinyl alcohol), a conductive filler (e.g., carbon), a defoaming agent, a buffer, or a combination of the foregoing.

The electrodes cannot be spaced so far apart that both the working electrode 20 and the dual-purpose reference/counter electrode 18 cannot be covered by the sample. It is preferred that the length of the path to be traversed by the sample (i.e., the sample path) be kept as short as possible in order to minimize the volume of sample required. The maximum length of the sample path can be as great as the length of the biosensor strip. However, the corresponding increase in resistance of the sample limits the length of the sample path to a distance that allows the necessary response current to be generated. The resistance of the sample is also influenced by the distance from the edge of the area of the dual-purpose reference/counter electrode 18 to the edge of the working area of the working electrode 20. Reducing this distance by positioning the dual-purpose reference/counter electrode 18 downstream from the working electrode 20 increases the resistance of the sample. Positioning the electrodes contiguously is conventional.

The trigger electrode 22 can be placed downstream of the reference electrode. The trigger electrode 22 can be used to determine when the sample has been applied to the strip, thereby activating the assay protocol. See U.S. Ser. No. 09/529,617, filed Jun. 7, 2000, incorporated herein by reference.

A biosensor strip 110 suitable for this invention is illustrated in FIG. 2. Referring to FIG. 2, an electrode support 111, preferably an elongated strip of polymeric material (e.g., polyvinyl chloride, polycarbonate, polyester, or the like) supports three tracks 112a, 112b, and 112c of electrically conductive ink, preferably comprising carbon. These tracks 112a, 112b, and 112c determine the positions of electrical contacts 114a, 114b, and 114c, a reference electrode 116, a working electrode 118, and a counter electrode 120. The electrical contacts 114a, 114b, and 114c are insertable into an appropriate measurement device (not shown) for measurement of current.

Each of the elongated portions of the conductive tracks 112a, 112b, and 112c can optionally be overlaid with a track 122a, 122b, and 122c of conductive material, preferably made of a mixture comprising silver particles and silver chloride particles. The enlarged exposed area of track 122b overlies the reference electrode 116. A layer of a hydrophobic electrically insulating material 124 further overlies the tracks 112a, 112b, and 112c. The positions of the reference electrode 116, the working electrode 118, the counter electrode 120, and the electrical contacts 114a, 114b, and 114c are not covered by the layer of hydrophobic electrically insulating material 124. This hydrophobic electrically insulating material 124 serves to prevent short circuits. The layer of hydrophobic electrically insulating material 124 has an opening 126 formed therein. This opening 126 provides the boundary for the reaction zone of the biosensor strip 110. Because this insulating material is hydrophobic, it can cause the sample to be restricted to the portions of the electrodes in the reaction zone. The working electrode 118 comprises a layer of a non-reactive electrically conductive material on which is deposited a layer 128 containing a working ink for carrying out an oxidation-reduction reaction. At least one layer of mesh 130 overlies the electrodes. This layer of mesh 130 protects the printed components from physical damage. The layer of mesh 130 also helps the sample to wet the electrodes by reducing the surface tension of the sample, thereby allowing it to spread evenly over the electrodes. A cover 132 encloses the surfaces of the electrodes that are not in contact with the electrode support 111. This cover 132 is a liquid impermeable membrane. The cover 132 includes a small aperture 134 to allow access of the applied sample to the underlying layer of mesh 130.

The layer of working ink 128 is deposited on that portion of the electrically conductive material of the working electrode 118 where the oxidation-reduction reaction is to take place when a sample is introduced to the biosensor strip 110. The layer of the working ink 128 can be applied to the working electrode 118 as a discrete area having a fixed length. Typical analytes of interest include, for example, glucose and ketone bodies. Typical non-reactive electrically conductive materials include, for example, carbon, platinum, palladium, and gold. A semiconducting material such as indium doped tin oxide can be used as the non-reactive electrically conductive material. In preferred embodiments, the working ink comprises a mixture of an oxidation-reduction mediator and an enzyme. Alternatively, instead of an enzyme, the working ink can contain a substrate that is catalytically reactive with an enzyme to be assayed. In the biosensor strips of this invention, the reagent(s) are preferably applied in the form of ink containing particulate material and having binder(s), and, accordingly, does not dissolve rapidly when subjected to the sample. In view of this feature, the oxidation-reduction reaction will occur at the interface of working electrode 118 and the sample. The glucose molecules diffuse to the surface of the working electrode 118 and react with the enzyme/mediator mixture.

In addition to being applied to the working electrode 118, a layer of the working ink can be applied to any of the other electrodes, when desired, as a discrete area having a fixed length.

Other possible biosensor strip designs include those in which the mesh layer 130 is eliminated, and the flow channel is of such dimensions that the biosensor strip takes up a liquid sample by capillary attraction. See U.S. Ser. No. 10/062,313, filed Feb. 1, 2002, incorporated herein by reference.

The mediator can be used for any NAD(P)$^+$dependent enzyme. Representative examples of these enzymes are set forth in Table 1.

TABLE 1

| E. C. (enzyme classification) Number | Enzyme name |
| --- | --- |
| 1.1.1.1 | Alcohol dehydrogenase |
| 1.1.1.27 | Lactate dehydrogenase |
| 1.1.1.31 | β-hydroxybutyrate dehydrogenase |
| 1.1.1.49 | Glucose - 6-phosphate dehydrogenase |
| 1.1.1.47 | Glucose dehydrogenase |
| 1.2.1.46 | Formaldehyde dehydrogenase |
| 1.1.1.37 | Malate dehydrogenase |
| 1.1.1.209 | 3-hydroxysteroid dehydrogenase |

Other enzyme systems that can be used with the mediator include, but are not limited to, oxidases (glucose oxidase, cholesterol oxidase, lactate oxidase). Formulations for screen-printing reagents on an electrode comprise the components set forth in Table 2 and Table 3, where % means % by weight.

TABLE 2

| (NAD)P$^+$ dependent enzyme (such as glucose dehydrogenase) | 200 to 4000 units per gram |
| --- | --- |
| Nicotinamide adenine dinucleotide (NAD) | 5 to 30% |
| 1,10-phenanthroline-5,6-dione | 0.1 to 1.5% |
| Filler (such as carbon or silica) | 10 to 30% |
| Binder (such as hydroxyethyl cellulose or guar gum or alginate) | 0.01 to 0.5% |
| Protein stabilizer (such as trehalose or bovine serum albumin) | 0.01 to 2% |
| Metal ion | 0.1 to 10% |
| Buffers and other electrolytes | 1 to 10% |

TABLE 3

| (NAD)P$^+$ dependent enzyme (such as glucose dehydrogenase) | 200 to 4000 units per gram |
| --- | --- |
| Nicotinamide adenine dinucleotide (NAD) | 5 to 30% |
| Metal complex of 1,10-phenanthroline-5,6-dione | 0.1 to 1.5% |
| Filler (such as carbon or silica) | 10 to 30% |
| Binder (such as hydroxyethyl cellulose or guar gum or alginate) | 0.01 to 0.5% |
| Protein stabilizer (such as trehalose or bovine serum albumin) | 0.01 to 15% |
| Buffers and other electrolytes | 1 to 10% |

The performance of biosensors for determining electrochemical ketone bodies can also be enhanced with the use of this chemistry. A typical formulation for determination of ketone bodies is shown in Table 4.

TABLE 4

| β-hydroxybutyrate dehydrogenase | 200 to 4000 units per gram |
| --- | --- |
| Nicotinamide adenine dinucleotide (NAD) | 5 to 30% |
| 1,10-phenanthroline-5,6-dione | 0.1 to 1.5% |
| Filler (such as carbon or silica) | 10 to 30% |
| Binder (such as hydroxyethyl cellulose or guar gum or alginate) | 0.01 to 0.5% |
| Protein stabilizer (such as trehalose or bovine serum albumin) | 0.01 to 2% |
| Metal ion | 0.1 to 10% |
| Buffers and other electrolytes | 1 to 10% |

In general, NAD(P)$^+$-dependent enzymes react with substrate according to the relationship

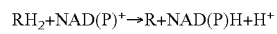

$$RH_2 + NAD(P)^+ \rightarrow R + NAD(P)H + H^+$$

NAD(P)H is oxidized back to NAD(P)$^+$ by the mediator described in this invention. The rate of this oxidation reaction is slower than that of other isomers (1,7-phenanthroline-5,6-dione and 4,7-phenanthroline-5,6-dione). This slow reaction rate prevents rapid regeneration of the coenzyme and hence makes it susceptible to variation in hematocrit or oxygen in the sample. The mediator will have higher probability of reacting with molecular oxygen and hence become sensitive to oxygen. The diffusion of the mediator in the sample is affected by the hematocrit variation and slow reacting mediator will be more affected by restricted mobility compared to a fast reacting mediator. The metal ions described herein allow rapid regeneration of the coenzyme and hence makes it less susceptible to variation in hematocrit or oxygen in the sample.

Figure 3:
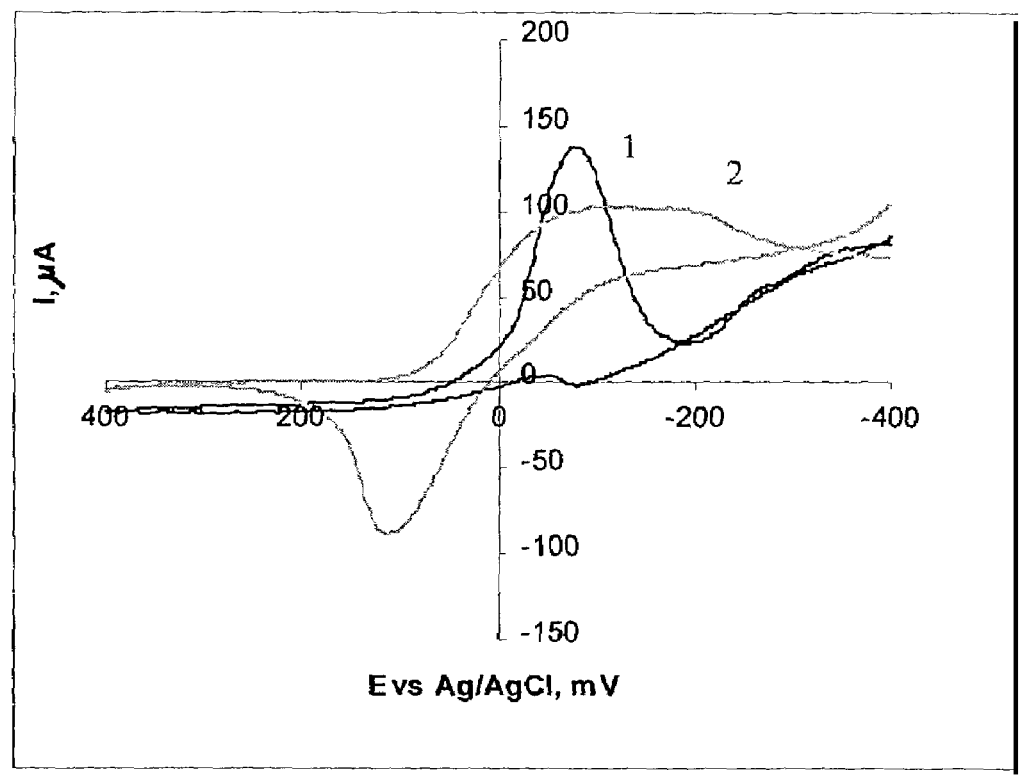
FIG. 3 is a graph showing electrochemical properties of 1,10-phenanthroline-5,6-dione in the absence of manganese chloride (Curve 1) and in the presence of manganese chloride (Curve 2).

Metal ion is required for efficient mediation of NADH oxidation by 1,10-phenanthroline-5,6-dione. In solution, 1,10-phenanthroline-5,6-dione does not show any electrochemical oxidation at physiological pH conditions. In the presence of a metal ion such as manganese, the mediator shows both oxidation and reduction current. FIG. 3 shows the electrochemical properties of 1,10-phenanthroline-5,6-dione in the presence of manganese chloride (Curve 2) and in the absence of manganese chloride (Curve 1).

The concentration of the metal ion required for the optimal performance of the biosensor depends on the binding constant of the metal and the 1,10-phenanthroline-5,6-dione. The efficiency of complex formation and stability of the complex is dependent on the metal ion. For example, only 10 mM manganese chloride is sufficient to achieve the performance that is achieved by a 360 mM magnesium chloride for 30 mM of 1,10-phenanthroline-5,6-dione in the formulation. Ten (10) mM manganese chloride corresponds to a ratio of one (1) metal ion to three (3) 1,10-phenanthroline-5,6-dione molecules in the formulation that forms the metal complex. The binding constant of Pb (II) with 1,10-phenanthroline-5,6-dione is greater than the binding constant of Mn (II) or Mg (II) with 1,10-phenanthroline-5,6-dione; however, the enzyme is inactivated by Pb (II). Mediation of NADH oxidation by 1,10-phenanthroline-5,6-dione in the presence of other transition metal ions and heavier alkaline earth metal ions has been demonstrated.

Transition metal ions and heavier alkaline earth metal ions can also be used as complexes for the mediation of NADH oxidation. The performance of the free ion Mn (II) mixed in the formulation is identical to the performance of the complex that is formed before it is added to the ink formulation.

Figure 4:
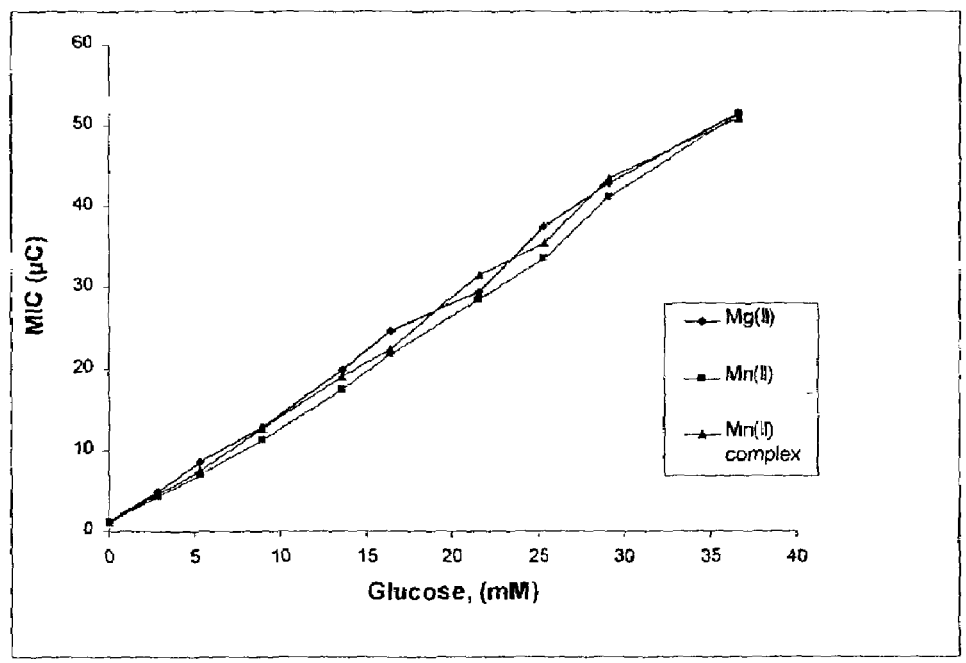
FIG. 4 is a graph showing the response of a biosensor as a function of the concentration of glucose for three formulations involving the mediator.
Figure 5:
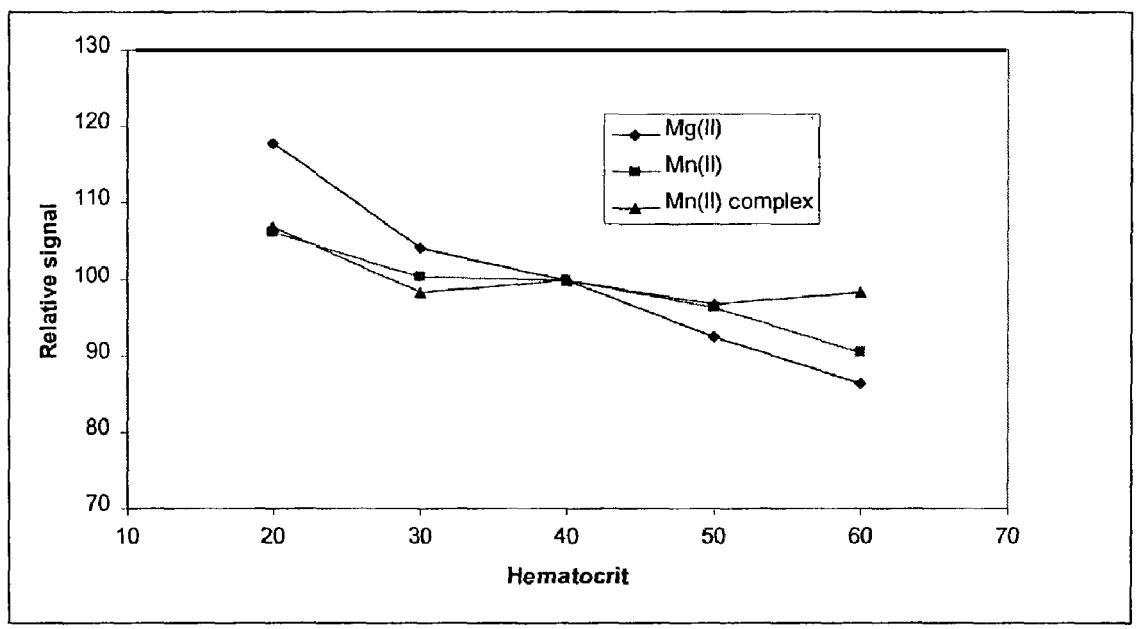
FIG. 5 is a graph showing the relative signals of biosensors for of glucose (15 mM sample) as a function of hematocrit for three formulations involving the mediator. The data are normalized to the signal at 40% hematocrit.
Figure 6:
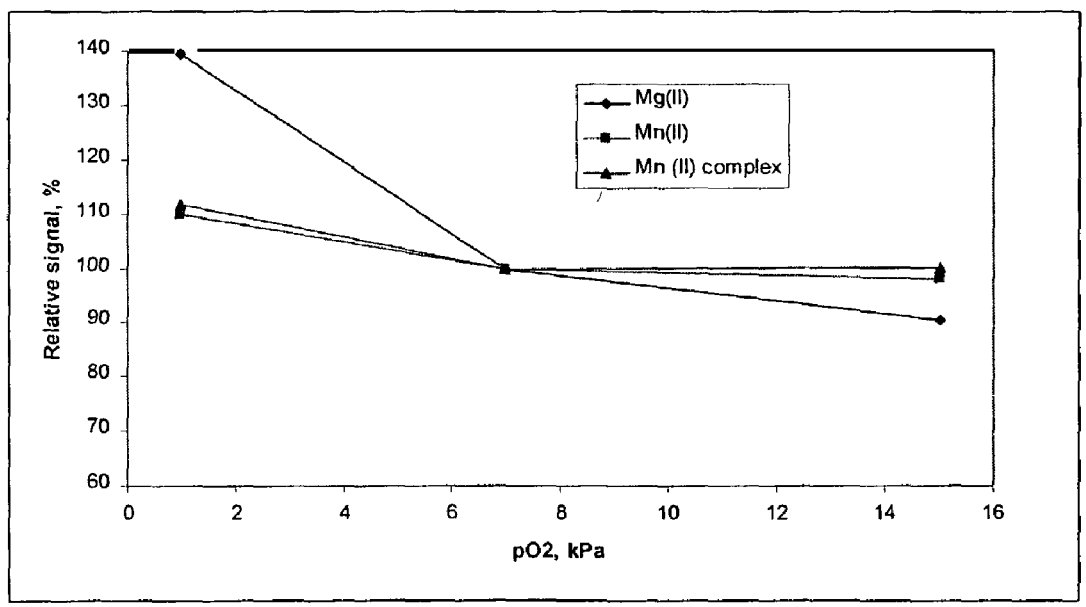
FIG. 6 is a graph showing the relative oxygen sensitivities of biosensors for three formulations involving the mediator. The data are normalized to 7 kPa.

The hematocrit and oxygen bias of formulations containing Mn (II) are significantly improved compared to the formulations containing Mg (II). FIG. 4 shows correlation of biosensor response as a function of concentration of glucose for the three mediation chemistries. FIG. 5 shows the relative signals of a 15 mM sample as a function of hematocrit normalized to the signal at 40% hematocrit. FIG. 6 shows oxygen sensitivities of the biosensors with three chemistries normalized to 7 kPa. Similar hematocrit and oxygen bias advantages are seen with the Fe (II) complex of 1,10-phenanthroline-5,6-dione. In other words, using a transition metal ion or a heavier alkaline earth metal ion in the formulation improves the electrochemical properties of the compound. Some of the transition metal ions and heavier alkaline earth metal ions show improved oxygen and hematocrit sensitivities as compared with other transition metal ions and heavier alkaline earth metal ions.

The complexes were either formed prior to use in the strip or the metal ions were mixed with the ink. The metal ions used were transition metal ions and heavier alkaline earth metal ions.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A biosensor strip comprising:
   (a) an electrode support;
   (b) a first electrode disposed on said electrode support, said first electrode being a working electrode, said working electrode comprising a working ink deposited on an electrically conductive material, wherein said working ink comprises an enzyme and complex comprising a mediator and at least one heavier alkaline earth metal ion, wherein said mediator is 1,10-phenanthroline-5,6-dione or a derivative thereof;
   (c) a second electrode disposed on said electrode support, said second electrode being a reference electrode; and
   (d) a third electrode disposed on said electrode support, said third electrode being a counter electrode, said counter electrode comprising an electrically conductive material.

2. The biosensor strip of claim 1, wherein said at least one metal ion is selected from the group consisting of calcium, strontium, and barium ion.

3. The biosensor strip of claim 1, wherein said enzyme is selected from the group consisting of glucose oxidase and glucose dehydrogenase.

4. The biosensor strip of claim 1, wherein said enzyme is NAD(P)$^+$-dependent dehydrogenase.

5. The biosensor strip of claim 1, further comprising a covering layer defining an enclosed space over said electrodes, said covering layer having an aperture for receiving a sample into said enclosed space.

6. The biosensor strip of claim 5, further comprising a least one layer of mesh interposed in the enclosed space between said covering layer and said electrodes.

7. The biosensor strip of claim 1, wherein said counter electrode is positioned relative to said working electrode and said reference electrode such that a liquid sample will contact said working electrode and said reference electrode prior to contacting said counter electrode.

8. A method for determining the concentration of an analyte in a sample of biological fluid, said method comprising the steps of:
   (a) providing the biosensor strip of claim 1;
   (b) inserting said biosensor strip into an analyte monitor;
   (c) applying said biological fluid to said biosensor strip;
   (d) applying a voltage at the working electrode with respect to the reference electrode;
   (e) measuring the current flowing between the working electrode and the counter electrode; and
   (f) correlating the current measured to the concentration of said analyte.

9. A biosensor strip comprising:
   (a) an electrode support;
   (b) a first electrode, said first electrode being a working electrode, said working electrode comprising working ink deposited on an electrically conductive material, wherein said working ink comprises an enzyme and a complex comprising a mediator and at least one heavier alkaline earth metal ion, wherein said mediator is 1,10-phenanthroline-5,6-dione or a derivative thereof;
   (c) a second electrode, said second electrode being a dual-purpose reference/counter electrode.

10. The biosensor of claim 9, wherein said at least one heavier alkaline earth metal ion is selected from the group consisting of calcium, strontium, and barium ions.

11. The biosensor strip of claim 9, wherein said enzyme is selected from the group consisting of glucose oxidase and glucose dehydrogenase.

12. The biosensor strip of claim 9, wherein said enzyme is NAD(P)$^+$-dependent dehydrogenase.

13. The biosensor strip of claim 9, wherein said electrode arrangement further includes a trigger electrode.

14. A method for determining the concentration of an analyte in a sample of biological fluid, said method comprising the steps of:
   (a) providing the biosensor strip of claim 9;
   (b) applying said biological fluid to said biosensor strip;
   (c) inserting said biosensor strip into an analyte monitor;
   (d) applying a voltage at the working electrode with respect to the dual-purpose reference/counter electrode;
   (e) measuring the current flowing between the working electrode and the dual-purpose reference/counter electrode; and
   (f) correlating the current measured to the concentration of said analyte.

15. A biosensor strip comprising:
   (a) an electrode support;
   (b) an electrode arrangement comprising at least two electrodes, one of said at least two electrodes being a working electrode, said working electrode disposed on said electrode support, said working electrode comprising a reaction layer comprising an enzyme and a complex comprising a mediator and at least one heavier alkaline earth metal ion, wherein said mediator is 1,10-phenanthroline-5,6-dione or a derivative thereof;
   (c) another of said at least two electrodes being a counter electrode, said counter electrode disposed on said electrode support.

16. The biosensor strip of claim 15, wherein said at least one metal ion is selected from the group consisting of calcium, strontium, and barium ions.

17. The biosensor strip of claim 15, wherein said enzyme is selected from the group consisting of glucose oxidase and glucose dehydrogenase.

18. The biosensor strip of claim 15, wherein said enzyme is NAD(P)$^+$-dependent dehydrogenase.

19. A method for determining the concentration of an analyte in a sample of biological fluid, said method comprising the steps of:

(a) providing the biosensor strip of claim 15;
(b) inserting said biosensor strip into an analyte monitor;
(c) applying said biological fluid to said biosensor strip;
(d) applying a voltage at the working electrode with respect to the counter electrode;
(e) measuring the current flowing between the working electrode and the counter electrode; and
(f) correlating the current measured to the concentration of said analyte.

* * * * *